United States Patent [19]
Kleinburg et al.

[11] Patent Number: 5,299,053
[45] Date of Patent: Mar. 29, 1994

[54] VARIABLE SHUTTER ILLUMINATION SYSTEM FOR MICROSCOPE

[75] Inventors: Larry Kleinburg, North Hollywood; Michael J. Danley, Temple City, both of Calif.

[73] Assignee: American Cyanamid Company, Wayne, N.J.

[21] Appl. No.: 604,699

[22] Filed: Oct. 26, 1990

[51] Int. Cl.$^5$ .................. G02B 26/02; G02B 21/06; A61B 3/08; A61B 3/10
[52] U.S. Cl. .................. 359/227; 359/233; 359/385; 351/201; 351/214; 351/246
[58] Field of Search .................. 350/507–528, 350/266–275, 6.5; 351/205–214, 221, 200, 201, 246, 242, 243; 359/227–236, 368, 369, 385–390, 900, 381; 250/232, 235–237 R

[56] References Cited

U.S. PATENT DOCUMENTS

| | | | |
|---|---|---|---|
| 3,814,510 | 6/1974 | Adler et al. | 359/246 |
| 4,063,807 | 12/1977 | Gelius et al. | 351/226 |
| 4,073,576 | 2/1978 | Bastian | 350/273 |
| 4,256,363 | 3/1981 | Briones | 359/369 |
| 4,524,271 | 6/1985 | Parker | 359/234 |
| 4,541,697 | 9/1985 | Remjian | 351/205 |
| 4,561,731 | 12/1985 | Kley | 359/385 |
| 4,640,580 | 2/1987 | Schlesinger | 350/272 |
| 4,732,148 | 3/1988 | L'Esperance, Jr. | 350/6.5 |
| 4,927,253 | 5/1990 | Stuber et al. | 350/514 |
| 4,940,323 | 7/1990 | Downing | 351/242 |
| 5,042,915 | 8/1991 | Akutsu et al. | 359/234 |
| 5,099,363 | 3/1992 | Lichtmann | 359/385 |

FOREIGN PATENT DOCUMENTS

| | | |
|---|---|---|
| 3219503 | 5/1982 | Fed. Rep. of Germany . |
| 219503 | 12/1983 | Fed. Rep. of Germany ...... 350/523 |
| 251415 | 11/1987 | Fed. Rep. of Germany ...... 359/385 |
| 142314 | 6/1988 | Japan ...... 350/523 |
| 63-142314 | 6/1988 | Japan . |

OTHER PUBLICATIONS

M. Michels, P. Sternberg–Operating Microscope-Induced Retinal Phototoxicity... Survey of Ophthalmology, vol. 34, No. 4 Jan./Feb. 1990 pp. 237–252.
M. Yanoff, F. Kurata, M. LaMensdorf–Inexpensive Device to Reduce Surgical Light Exposure Ophthalmology–Instrument & Book Supplement 1983 pp. 137 & 138.
D. J. McIntyre–Phototoxicity McIntyre–The Eclipse Filter Nov., 1983 pp. 364 & 365.

*Primary Examiner*—Bruce Y. Arnold
*Assistant Examiner*—Thong Nguyen
*Attorney, Agent, or Firm*—Brian R. Woodworth

[57] ABSTRACT

An opthalmic microscope is provided having a variable shutter illumination system which decreases the amount of light from the light source passing through the shutter to the field of view. When a patient's eye is positioned within the field of view, the variable shutter acts to decrease the exposure time the illumination beam contacts a patient's retina. In a first embodiment, the variable shutter includes a rotating disk having at least one controllable operative where such disk is placed between the illumination source and the field of view of the microscope. In another embodiment, the variable shutter is provided by an electronically controlled liquid crystal shutter which is operable between a fully open position allowing substantially all of the light beam to pass therethrough to a fully closed position totally blocking the transmission of light through the shutter.

7 Claims, 3 Drawing Sheets

VARIABLE SHUTTER ILLUMINATION SYSTEM FOR MICROSCOPE

TECHNICAL FIELD

The present invention relates to microscopes adapted primarily for ophthalmic surgical procedures and, more particularly, to microscopes having a variable shutter illumination system to decrease the amount of light reaching a patient's retina during an ophthalmic surgical procedure.

BACKGROUND OF THE INVENTION

The concept of light-induced retinal damage has been recognized since the time of Plato, and was first clinically studied as early as 1916 as discussed in an article titled "Pathological Effects of Radiant Energy on the Eye" by Dr. F. H. Verhoeff, et al. printed in *Proc. Am. Acad. Arts Sci,* Volume 51, pages 629-818 (1916). The article describes the nature of solar burns affecting the retinal pigment epithelium and choroid. However, at that time, they attributed this damage to an increase in ocular temperature and not to an overstimulation of the retina with light.

It was not until experimental work performed in the mid 1960's that nonthermal retinal light damage became recognized. The myth that such damage could be caused only by intense light sources, such as the sun and various photocoagulators, gave way to reality that damage from lower intensity light was probable and that additivity of several exposures was possible.

And, in the last twenty years, the prior art is replete in describing how commonly-used ophthalmic devices and microscopes can cause experimental light damage in animal models. In the last fifteen years, the use of intense light sources in ophthalmic surgery has increased. And, recently, there have been numerous reports of iatrogenic phototoxicity following routine cataract extraction, epikeratophakia, combined anterior segment procedures, and vitrectomy surgery.

The term "phototoxicity" or "phototoxic lesion" is usually employed to describe the typical retinal lesion produced after a relatively short intense exposure to a light source such as the operating microscope.

In an article by Dr. D. M. Robertson et al., entitled "Photic Retinopathy from the Operating Room Microscope", printed in the *American Journal of Ophthalmology,* Volume 101, pages 452 ∝ 462 (1986), it was conclusively established that a cause and effect relationship exists between exposure to the operating microscope light and retinal or phototoxic lesions. Evidence also exists that light from the operating microscopes contributes to post-operative cystoid macular edema (CME).

A number of factors attribute to the occurrence of phototoxicity or CME in patients during an ophthalmic operation. And, since retinal damage is largely a function of these factors such as light power, exposure time, and wave length of the light, a reduction of total energy delivered to the retina throughout an entire procedure can be accomplished in various manners.

Filtration is one method of limiting the damaging light rays from reaching the retina. Retinal susceptibility to phototoxic effects is greatest at the blue-violet end of the light spectrum. Consequently, filtration that is cut off below 400-450 mm may be added to the microscope illumination system. However, this may be unnecessary where glass fiber bundles or cables are used to transfer light to the microscope because the ultraviolet absorption characteristics of glass cause the glass bundles to provide for a very effective ultraviolet absorption automatically, perhaps making further filtration unnecessary on fiberoptic-equipped microscopes.

Oblique illumination, rather than coaxial illumination, may decrease the power of the light reaching the retina. Oblique illumination will place the intense image of the illuminating beam in the far periphery of the retina, thus protecting the posterior pole. However, the commonly available oblique illumination attachments are somewhat inconvenient, cause vignetting of photo/video images and also increase the length of the microscope body.

Defocusing the illumination beam on the retina by insertion of an air bubble in the anterior chamber will increase the size and, thus, decrease the intensity of the illumination beam as it falls on the retina. However, the amount of defocusing varies greatly with the size of the bubble and it is unclear on whether this procedure would help prevent phototoxicity.

Another manner of preventing phototoxicity is to limit the exposure time the microscope illumination system is projecting its beam of light on a patient's retina. Two methods of minimizing total light energy by decreasing exposure time to the brightest light have been disclosed in the prior art.

First, Dr. Yanoff et al., in an article entitled, "Inexpensive Device to Reduce Surgical Light Exposure", as printed in *Ophthalmology,* Volume 90, (Instrument and Book Supplement), pages 137-138 (1983), discloses a rubber cap which is placed over the cornea after a cataract removal to cover the visual axis and remains in place during the final closure of the wound. A second approach is discussed in an article by Dr. D.J. McIntyre entitled, "Phototoxicity — The Eclipse Filter", as printed in *Ophthalmology,* Volume 92, pages 364-365 (1985), wherein he discusses the use of a movable opaque disk which can be placed in the appropriate plane of the illumination system of the microscope to project a sharply-focused black spot of 11 mm in diameter. The surgeon can place the black spot over the pupil when he does not need direct illumination of the retina and raises the spot away from the pupil when he does need to direct the illumination beam onto the retina. However, both methods use devices which block not only the microscope illumination beam but also the surgeon's sight of the retina during an ophthalmological operation.

It is, therefore, one object of the present invention to provide a microscope having an illumination system or module which decreases the amount of light passing through it over time without interrupting a surgeon's full field of vision through the microscope.

It is another object of the present invention to provide a microscope illumination system having a variable shutter means so as to allow a surgeon to adjust the amount of light that is blocked from striking the patient's retina.

It is a further object of the present invention to provide a microscope having a variable shuttered illumination system capable of reducing the occurrence of phototoxicity in patients undergoing an ophthalmic surgical operation.

It is still a further object of the present invention to provide a microscope having a variable shuttered illumination system capable of reducing the occurrence of postoperative cystoid macular edema (CME) in patients undergoing an ophthalmic surgical operation.

Another object of the present invention is to provide a microscope having a variable shuttered illumination system to reduce the amount of light striking a patient's retina during an ophthalmic surgical operation without restricting the surgeon's field of vision so as to reduce the occurrence of postoperative retinal damage to the patient.

SYSTEM OF THE INVENTION

Accordingly, the present invention is an ophthalmic microscope having a variable shutter illumination system which decreases the amount of light passing through the shutter so as to decrease the exposure time such light is contacting a patient's retina.

The microscope itself is well-known in the art and is utilized by an ophthalmic surgeon to view the details of a patient's eye, such as the retina, while performing an ophthalmic surgical operation. It is necessary for such a microscope to utilize a light source to properly illuminate the field of view for the surgeon operating the microscope. This light source can also be utilized to provide sufficient light for a documentation module (camera) to record the surgical operation for viewing at a later date. As discussed above, it is desirable to provide a shutter device within the illumination system to reduce the patient's exposure to the light rays of the illumination system to reduce the risk of postoperative phototoxicity or CME.

The variable shutter of the illumination system provides a rotating disk or shutter placed between the illumination source and the objective lens of the microscope for projection of light rays onto an image to be viewed by the surgeon. The shutter is initially set at a 50% duty cycle which means that for every revolution of the shutter, the light is blocked 50% of the time and allowed to pass through the open portion of the shutter 50% of the time. The shutter or disk includes a variable shutter blade which can be mechanically rotated on the disk to further close down the aperture through which light may pass by the rotating shutter. The variable shutter is rotated by an electric motor at speeds of 30 revolutions per second or greater so that the surgeon using the microscope will not see any flickering of the lightbeam while performing the operation. In this manner, the device of the present invention will decrease the patient's exposure to any harmful effects of the illumination system while providing a seemingly constant light source for the surgeon utilizing the microscope.

An alternate embodiment discloses a microscope having an electronically-controlled liquid crystal shutter to provide the variable shutter illumination system. In this alternate embodiment, an electronic circuit is utilized to activate a liquid crystal from an open position allowing light to pass through the crystal to a fully-closed position totally blocking the transmission of light through the crystal. The circuitry can be utilized to alternatively open and close the liquid crystal to the transmission of light therethrough in such a manner that, like the rotating shutter discussed above, the patients exposure to any harmful effects of the intense light of the microscope illumination system will be decreased while providing a seemingly constant light source to the image (or patient's eye) for viewing by the user of the microscope.

These and other objects and advantages of the present invention will become more fully apparent by a complete reading of the following detailed description, the appended claims thereto, and the accompanying drawings.

DETAILED DESCRIPTION OF THE INVENTION

Figure 1:
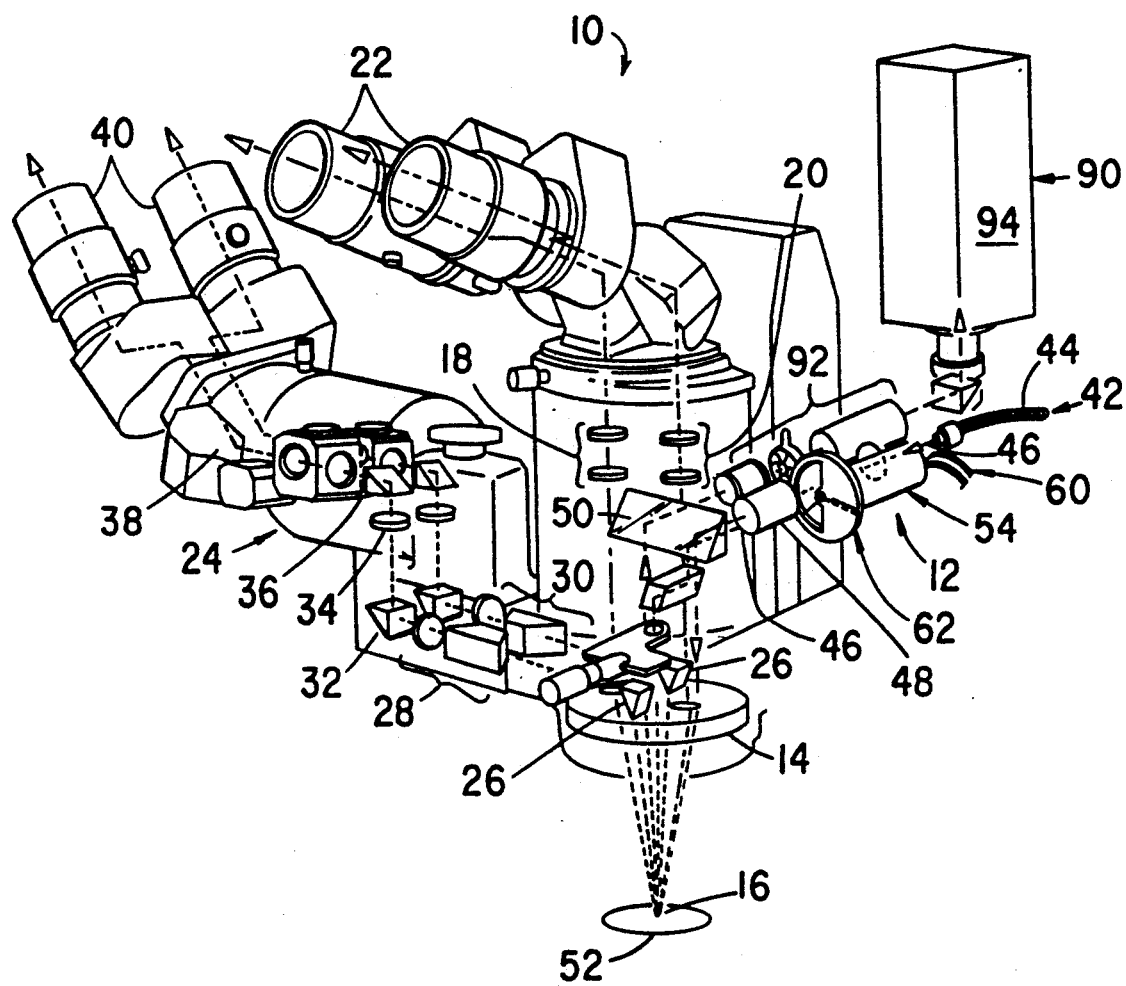
FIG. 1 is a schematic diagram of the microscope of the present invention illustrating the use of an illumination system having a variable shutter means.

Referring to FIG. 1, a schematic diagram of a typical microscope 10 for use with the variable shutter illumination system 12 of the present invention is shown. A typical ophthalmic microscope 10 includes an objective lens 14 in spaced relationship to an image 16 to be viewed. A typical objective lens may be found in U. S. Pat. No. 4,688,907, issued Aug. 25, 1987, in the name of Larry K. Kleinberg, which is hereby incorporated by reference. Two pairs of laterally-spaced lenses 18 and 20 are disposed vertically above the objective lens 14. A set of stereo eye pieces 22, for use by the primary surgeon, view the image 16 by rays of light which pass through the objective lens 14 and lenses 18 and 20 to the stereo eye pieces 22. Any type of commonly used or known stereo microscope can be used in accordance with the present invention.

The microscope shown in FIG. 1 further shows an observer's secondary viewing station 24. The secondary viewing station 24 generally includes a pair of triangular right angle prisms 26 disposed adjacent the objective lens 14. The prisms 26 are rotatable about their longitudinal axes for a total angle of approximately ninety degrees (90°). The prisms 26 redirects the rays of light from the image 16 at ninety degrees (90°) in the unused portion of the objective lens 14. The secondary viewing station 24 includes a number of optical lenses 28 and 30 laterally spaced from the prisms 26. A second pair of generally triangular right angle prisms 32 are disposed laterally of the lenses 30. Another pair of lenses 34 are spaced vertically above the prisms 32. The optical train of the secondary viewing station 24 further includes another two pairs of triangular right angle prisms 36 and 38 spaced along the axes of the light path of the secondary viewing station 24. A second set of stereo eye pieces 40 for use by an assisting surgeon, student or nurse also views the image 16 by rays of light which pass through the objective lens 14 and optical light path as described above to the sterio eye pieces 40.

The observer's secondary viewing station 14 preferably is the same as the station illustrated and described in U.S. application Ser. No. 554,325, filed on Jun. 27, 1990, which application is a Continuation-in-Part of U. S. Pat. No. 4,938,575. The disclosures of both the '325 application and '575 patent are herein incorporated by reference. It is also understood that other secondary viewing stations of standard or conventional type can be used which satisfy the objects of the present invention. It is also understood that the present invention can be practiced without the use of a secondary viewing station.

Referring to FIG. 1 and, particularly, to FIGS. 2-8 wherein the attributes of the present invention are discussed in greater detail, FIG. 1 further illustrates the variable shutter illumination system or module 12 of the present invention. And, in FIGS. 2 and 3, the variable shutter illumination module 12 of the present invention is generally shown to transmit light from a light source 42 through a fiberoptic cable 44 to the variable shutter illumination module 12. The light path 46 is emitted from the fiberoptic cable 44 and passes through the variable shutter mechanism of module 12. The light path 46 continues through a series of lenses 48 and a right angle prism So into and through the objective lens 14 to the field of view 52. Reflected light is transmitted back through the objective lens 14 to both the first and second pairs of stereo eye pieces 22 and 40, respectively.

Figure 2:
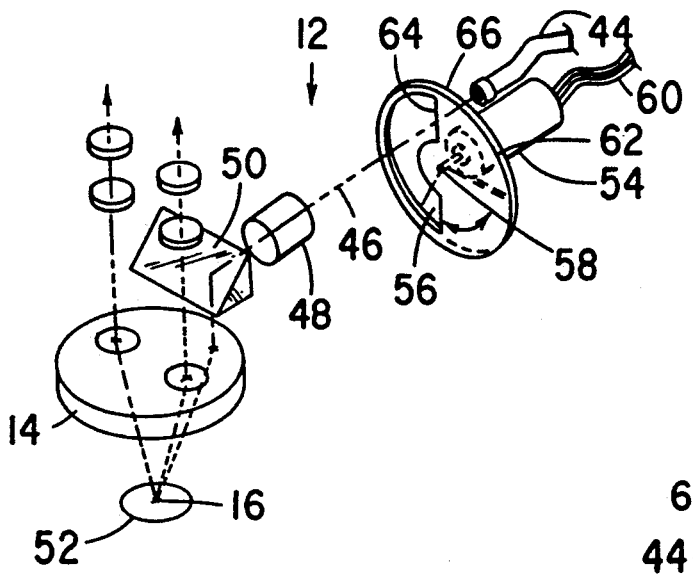
FIG. 2 is a schematic diagram of a network of optical elements or prisms forming the variable shutter illumination system according to the present invention.

As further shown in FIG. 2, the variable shutter mechanism includes an electric motor 54 having a rotating shaft 58. The motor 54 is controlled via an electric power source (not shown) through wires 60. A shutter or disk 62 is attached to the motor shaft 58; the disk 62 having a semi-circular cutout 64 for approximately one-half the surface area of disk 62. A continuous rim 66 surrounds the semi-circular cutout 64 to give the disk 62 added strength. The disk 62 is shown in FIG. 2 as having a cutout 64 representing approximately one-half of the surface area of disk 62. This shutter would therefore operate on a 50% duty cycle which means that, for every rotation, the light path 46 would be blocked by the disk for one-half of the time and be allowed to pass through the disk one-half of the time.

As shown in FIG. 2, the disk 62 is placed within the light path 46 between the fiberoptic cable 44 and lenses 48. The disk 62 is rotated by motor 54 at relatively high speeds in the order of thirty (30) revolutions per second such that a surgeon utilizing either of the stereo eye pieces would not see the light flicker or any other indication that the light path 46 is in any way being interrupted by the spinning disk.

Figure 3:
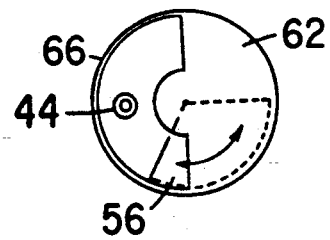
FIG. 3 is a front plan view of the rotating disk and variable shutter blade of FIG. 2, with the blade shown in the partially closed position of the disk openings.

Referring to FIG. 3, a variable shutter blade 56 is shown attached to the disk 62 to allow the surgeon to decrease the duty cycle to below 50% to further decrease the amount of light reaching the field of view 52. The blade 56 can be mechanically rotated relative to the disk 62. The variable shutter blade can be attached to the disk in a manner known in the art such that the blade 56 can be manually adjusted to change the size of the disk cutout 64 as desired by the operator of the microscope.

Figure 4:
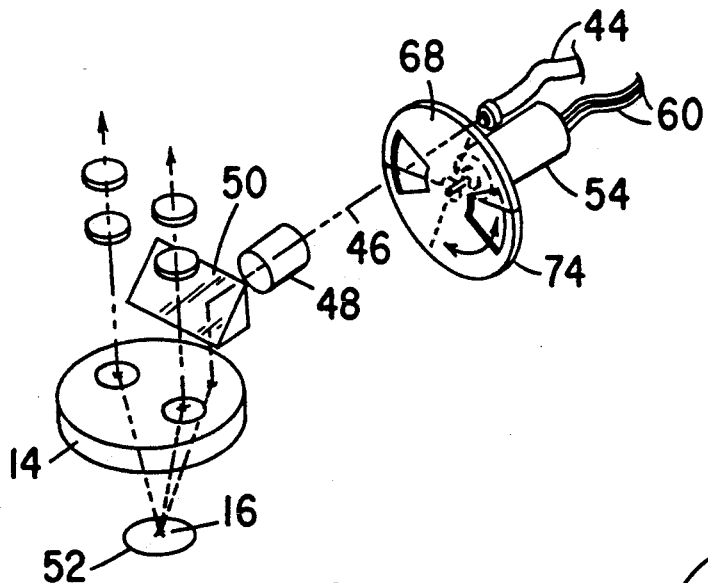
FIG. 4 is a schematic diagram of a network of optical elements or prisms forming the variable shutter illumination system utilizing an alternate embodiment of the variable shutter means of the present invention.
Figure 5:
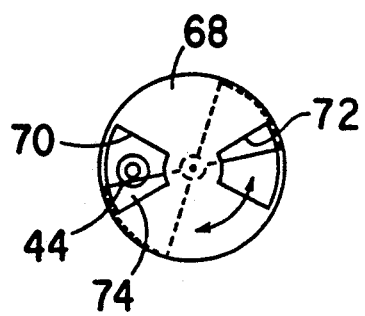
FIG. 5 is a front plan view of the alternate disk and variable shutter blade of FIG. 4.

FIGS. 4 and 5 illustrate a second embodiment of the variable shutter mechanism wherein a disk 68 of an alternate configuration is shown. Disk 68 has two cutouts, 70 and 72, diametrically opposed to each other. Light within the light path 46 is allowed to pass through disk 68 only when one of the two cutouts, 70 or 72, is positioned as shown in FIG. 4 and 5. Disk 68 also includes a variable or movable shutter blade 74 which can be rotated in relation to the disk 68 and its cutouts 70 and 72 to further decrease the mechanisms duty cycle as discussed above. The movable shutter blade 74 can be attached to the disk 68 in the same manner as discussed above.

Figure 6:
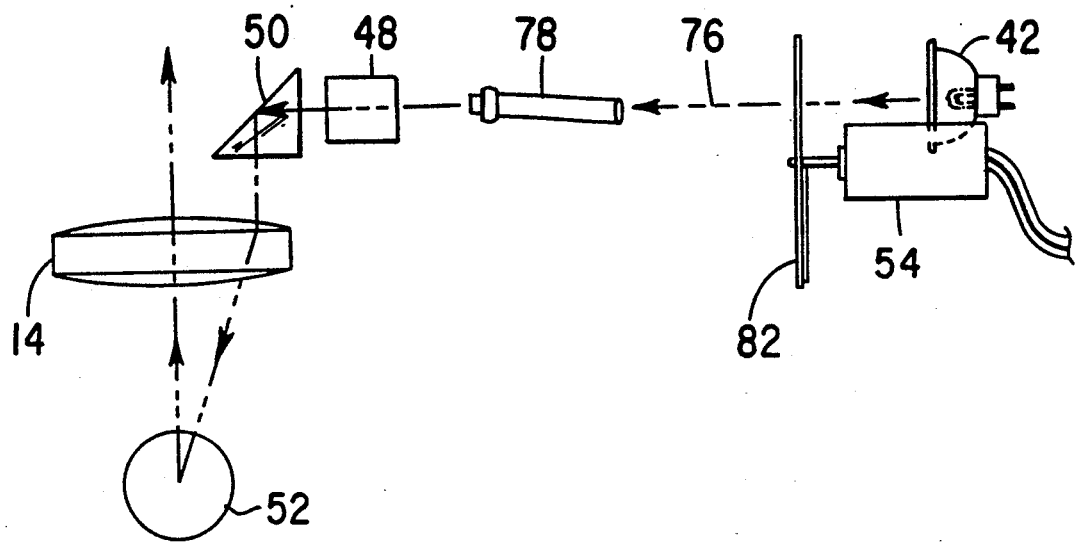
FIG. 6 is a partial side view of an alternate embodiment of the variable shutter illumination system of the present invention illustrating the variable shutter means being placed adjacent the light source.

FIG. 6 shows another embodiment of the invention wherein the motor 54 and disk 82 are placed immediately adjacent the light source 42. The light path 76 then proceeds into a fiberoptic cable 78 and through lenses 48 and the right angle prism 50, objective lens 14 to the field of view 52.

Figure 7:
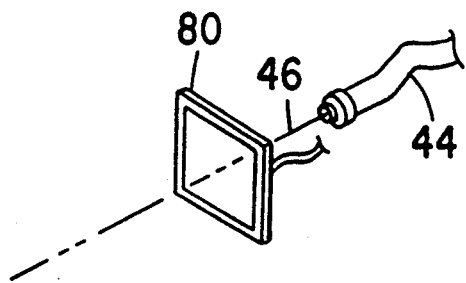
FIG. 7 is a schematic diagram illustrating an alternate embodiment of the variable shutter illumination system of the present invention utilizing a liquid crystal shutter.
Figure 8:
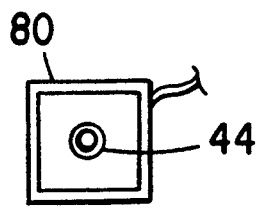
FIG. 8 is a front-plan view of the variable liquid crystal shutter of FIG. 7.

There are also other possible variable shutter mechanisms which could be placed within the light path of the illumination source of the present invention. One such mechanism is shown in FIGS. 7 and 8 wherein a liquid crystal shutter 80 is placed within light path 46 or 76 (of rigs. 2 and 6, respectively) of the various embodiments of the present invention. Liquid crystal shutter 80 is activated by an electronic circuit (not shown) utilizing a square wave generator having a constant voltage output from zero to thirty volts with less than 25 millivolts bias. The period for the square wave would be set in such a manner to minimize the perception of light flicker with a 50% duty cycle. The liquid crystal shutter 80 can be opened and closed very quickly such that the on/off transition time is from between 100 microseconds to 1 millisecond. Such a liquid crystal shutter can be purchased from Hercules Aerospace Display Systems, Inc., 2374 North Penn Road, Hatfield, Pa.

The present invention, as shown in FIG. 1, may also utilize a document illumination module 90. Such a module 90 is generally described in U. S. Pat. No. 4,856,873. The disclosure of the '873 patent is herein incorporated by reference. It is also understood that other document illumination modules of conventional type can be used which satisfy the objects of the present invention. In module 90, reflected light passing through the variable shutter illumination system is transmitted back through the objective lens 14 and the prism So and through a focusing and shaping series of lenses 92 to a document recording mechanism 94. The recording mechanism 94 can be a video camera, photographic camera, or the like.

Various changes and modifications may be made in the variable shutter illumination system of the present invention. For example, the variable shutter may have larger or smaller openings than described herein to provide either larger or smaller duty cycles. Furthermore, the rotating shutter 62 may be spun at lower or greater revolutions per second as long as the surgeon using the microscope is unable to discern a flickering of the light or decrease in the intensity of the light during its operation.

The present invention has been described in an illustrative manner. It is to be understood that the terminology which has been used is intended to be in the nature of words of description rather than of limitation. Obviously, many modifications and variations of the present invention are possible in light of the above teachings. Therefore, within the scope of the appended claims, the present invention may be practiced otherwise than as specifically described.

What is claimed:

1. In a surgical microscope system having at least one eyepiece for viewing a field of view and having a source of illumination for providing a light beam to illuminate the field of view, the improvement comprising:

a shutter means positioned between the source of illumination and the field of view, said shutter means being constructed for continuously interrupting the light beam being transmitted to the field of view at a frequency greater than the flicker frequency of a human eye, said shutter means comprising a rotatable disk and a motor for rotating said rotatable disk, said rotatable disk having one or more apertures formed therethrough for transmittal of the light beam therethrough, whereby the light beam is partially blocked from reaching the field of view upon rotation of said rotatable disk, and whereby the exposure time of the light beam on the field of view is reduced without creating a humanly perceptible flickering of the light beam.

2. A surgical microscope system in accordance with claim 1, wherein said one or more apertures formed through said rotatable disk are dimensioned and disposed such that the light beam is blocked from reaching the field of view about fifty percent of the time.

3. A surgical microscope system in accordance with claim 2, wherein said rotatable disk defines a single aperture therethrough.

4. A surgical microscope system in accordance with claim 1, said shutter means further comprising a variable shutter blade disposed on said rotatable disk, said variable shutter blade being rotatable with respect to said rotatable disk and said one or more apertures defined through said rotatable disk, whereby a surface area defined by said rotatable disk and said variable shutter blade can be varied such that the amount of the light beam passing through said rotatable disk as said rotatable disk is rotated can be selectively varied to control the exposure time of the light beam on the eye.

5. An ophthalmic illumination system having a source of illumination for providing a light beam to illuminate a field of view of an eye, the improvement comprising:

a shutter means positioned between the source of illumination and the field of view, said shutter means being constructed for continuously interrupting the light beam being transmitted to the field of view at a frequency greater than the flicker frequency of a human eye, said shutter means comprising:

a rotatable disk, said rotatable disk having a plurality of apertures defined therethrough for transmitting of the light beam therethrough;

a motor for rotating said rotatable disk; and a variable shutter blade disposed on said rotatable disk, said variable shutter blade being rotatable with respect to said rotatable disk and said plurality of apertures defined through said rotatable disk, whereby a surface area defined by said rotatable disk and said variable shutter blade can be varied such that the amount of the light beam passing through said rotatable disk as said rotatable disk is rotated can be selectively varied to control the exposure time of the light beam on the eye.

6. A method for illuminating an eye with a light beam emanating from a source of illumination, said method comprising the steps of:

placing between the source of illumination and the eye a rotatable disk having one or more apertures defined therethrough for transmitting of the light beam therethrough; and rotating the rotatable disk such that the light beam is continuously interrupted at a frequency greater than the flicker frequency of the human eye is reduced without creating a humanly perceptible flickering of the light beam.

7. A method for illuminating an eye in accordance with claim 6, said method further comprising the steps of providing a variable shutter blade on the rotatable disk, said variable shutter blade being rotatable relative to the rotatable disk and said one or more apertures defined through said rotatable disk, and selectively positioning the variable shutter blade, whereby a surface area defined by said rotatable disk and said variable shutter blade selectively controls the amount of the light beam passing through said rotatable disk and illuminating the eye, thereby controlling the exposure time of the light beam on the eye.

* * * * *